US00PP34964P3

(12) United States Plant Patent
Smith

(10) Patent No.: US PP34,964 P3
(45) Date of Patent: Feb. 7, 2023

(54) MANDARIN TREE NAMED '12C009'

(50) Latin Name: *Citrus reticulata*
Varietal Denomination: 12C009

(71) Applicant: State of Queensland Through the Department of Agriculture and Fisheries, Brisbane (AU)

(72) Inventor: Malcolm W. Smith, Bundaberg (AU)

(73) Assignee: STATE OF QUEENSLAND THROUGH THE DEPARTMENT OF AGRICULTURE AND FISHERIES, Brisbane (AU)

( * ) Notice: Subject to any disclaimer, the term of this patent is extended or adjusted under 35 U.S.C. 154(b) by 0 days.

(21) Appl. No.: 17/546,834

(22) Filed: Dec. 9, 2021

(65) Prior Publication Data

US 2022/0201911 P1 Jun. 23, 2022

Related U.S. Application Data

(60) Provisional application No. 63/128,532, filed on Dec. 21, 2020.

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./201, 202
See application file for complete search history.

(56) References Cited

U.S. PATENT DOCUMENTS

2021/0251118 P1 * 8/2021 Smith ..... Plt./202

* cited by examiner

*Primary Examiner* — Susan McCormick Ewoldt
(74) *Attorney, Agent, or Firm* — Morrison & Foerster LLP

(57) ABSTRACT

A new and distinct variety of mandarin tree named '12C009', particularly selected for non-acidic flavour profiles and distinguished by the smooth skin texture, cleanness of peeling and high Brix levels, is disclosed.

3 Drawing Sheets

Latin name: Botanical classification: *Citrus reticulata.*

Varietal denomination: The varietal denomination of the claimed variety of mandarin tree is '12C009'.

BACKGROUND OF THE INVENTION

Mandarin is an important and valuable commercial fruit crop. Accordingly, there is a need for new varieties of mandarin trees. In particular, there is a need for improved varieties that can be harvested late in the season and meet consumer expectations for attractive external appearance (e.g. color and smoothness) combined with good eating qualities (e.g. sweet and low-seeded).

SUMMARY OF THE INVENTION

In order to meet these needs, the present invention is directed to an improved variety of mandarin tree. In particular, the invention relates to a new and distinct variety of mandarin tree (*Citrus reticulata*), which has been denominated as '12C009'.

The initial step in the invention involved selection from a breeding population of approximately 6,000 hybrids between the female parent 'Ellendale' (unpatented) and the male parent 'Murcott' (unpatented), which was made in 2002. Following this, the material was subject to mutation breeding using a cobalt 60 gamma cell on two occasions during 2008. A small number of buds survived this treatment and developed into nursery trees suitable for field planting. A total of 147 such nursery trees (many of them doublebudded) were planted at four different field sites between late 2009 and early 2011. Fruit on individual branches were checked for seed number as these trees started to come into production. '12C009' was identified as an individual branch mutation in January 2009 and asexually reproduced onto 'Troyer' (unpatented) rootstocks in February 2009 at a research station in Bundaberg, Queensland, Australia, by taking young stems from the identified branch, removing individual buds from these young stems, and budding them onto the 'Troyer' rootstocks. A total of 141 asexually reproduced trees resulted (propagated from budwood taken off the original individual branch mutation) and were field-planted at four different sites in Queensland, Australia, namely in the regions of Bundaberg, Gayndah, Mundubbera, and Boyne. Trees at all four sites have shown stability in all traits, with a phenotype consistent with the original individual branch mutation. Trees propagated by collecting budwood from the four different field sites in 2012 have also shown consistency with the original phenotype, demonstrating stability across two generations of asexual reproduction and multiple (4) testing sites. Observation and testing of the 141 trees planted at these four sites in central Queensland, together with annual assessment (12 years) of the original limb identified in 2009, confirmed the stable retention of distinct characteristics of '12C009'.

'12C009' trees produce moderate crops of medium to large fruit that mature toward the end of the commercial mandarin harvest season (end of July in Queensland, Australia). To date, '12C009' has similar productivity to existing commercial mandarin cultivars. The fruit are firm and yet still relatively easy to peel, and the skin texture is smooth and without a prominent neck at the stem end. The fruit peel cleanly and have low seed numbers. High Brix levels are balanced with moderate acidity giving a sweet flavor well suited to Asian markets that prefer non-acidic fruit. Simulation experiments indicate that this invention is suitable for long-distance shipping while retaining its distinct mandarin characteristics.

'12C009' differs from the female parent 'Ellendale' in that '12C009' has smoother fruit skin, lower seed numbers per fruit, polyembryonic seed, lower pollen viability, later fruit maturity time, absence of a navel, absence of a neck on the fruit, and susceptibility to *Alternaria* brown spot disease, as compared to 'Ellendale'. '12C009' differs from the male parent 'Murcott' in that '12C009' has better peel color, lower seed numbers per fruit, lower pollen viability, being easier to peel, and a flatter, less rounded fruit shape, as compared to 'Murcott'.

'12C009' is most closely comparable to mandarin variety '11C017R' (U.S. Plant Pat. No. 34,166) in that '12C009' and '11C017R' both have smooth skin texture, high Brix levels, low seed numbers, being easy to peel, and being from the same parentage. However, '12C009' is markedly different from '11C017R' in that '12C009' has polyembryonic seeds and a maturity time that is at least 6 weeks later than '11C017R'. Further, juice from '11C017R' is around 0.48% citric acid equivalent in the middle of June, while '12C009' still has a high acidity (0.95%) at the end of July.

'12C009' was particularly selected for its later maturity time.

BRIEF DESCRIPTION OF THE DRAWINGS

Mandarin tree variety '12C009' is shown in the accompanying photographs, illustrating typical fruit external and internal appearance, uniformity and tree productivity. The illustrated trees and fruit were grown under subtropical conditions in central Queensland, Australia and colors are as true as can be captured photographically. Field photographs are of plants that are four years old.

DETAILED BOTANICAL DESCRIPTION

Figure 1:
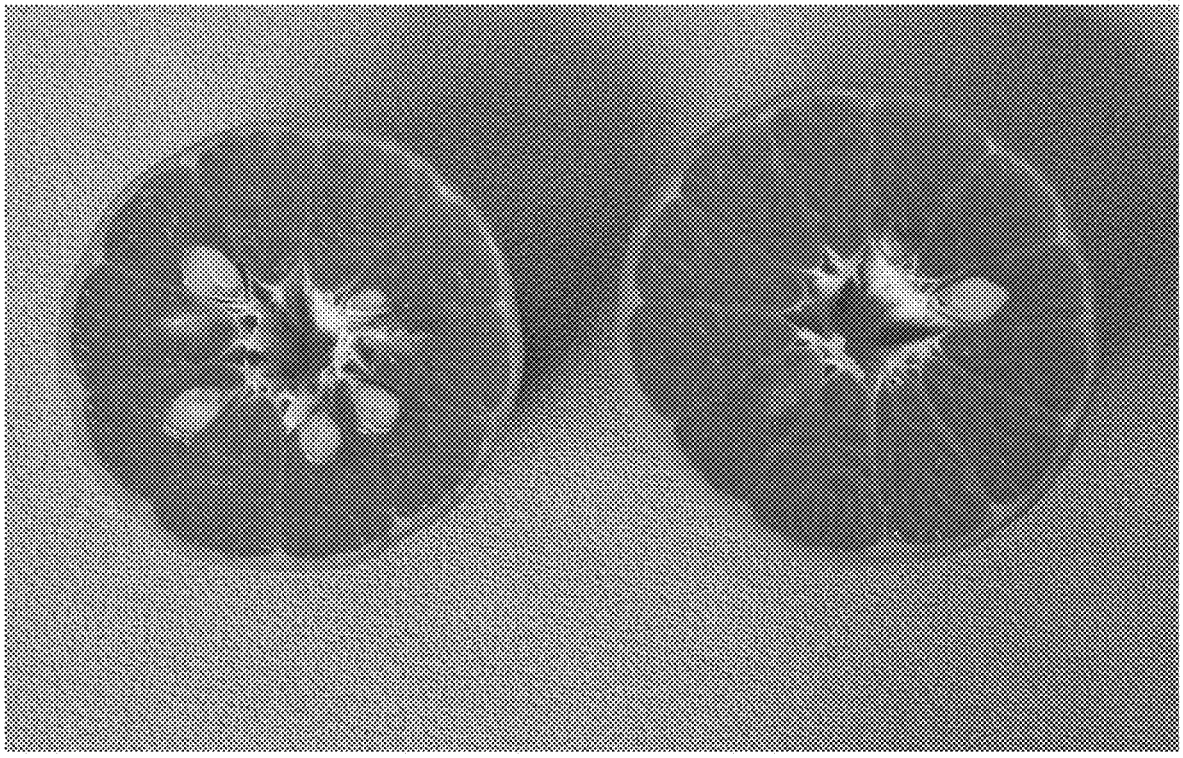
FIG. 1 shows fruit cross-section of '12C009' (right panel) compared to the progenitor with higher seed numbers (left panel) used during the two rounds of mutation breeding.
Figure 2:
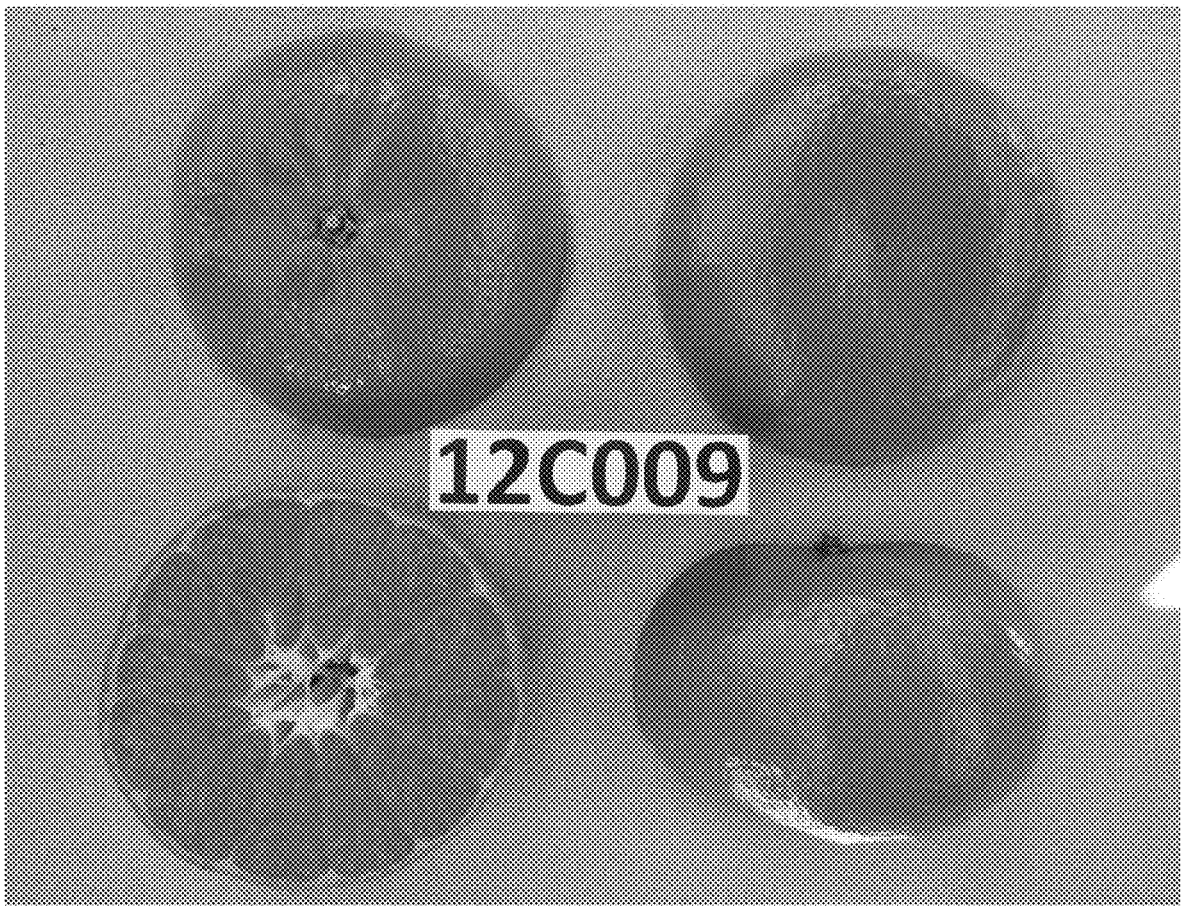
FIG. 2 shows fruit of '12C009' from four different angles.
Figure 3:
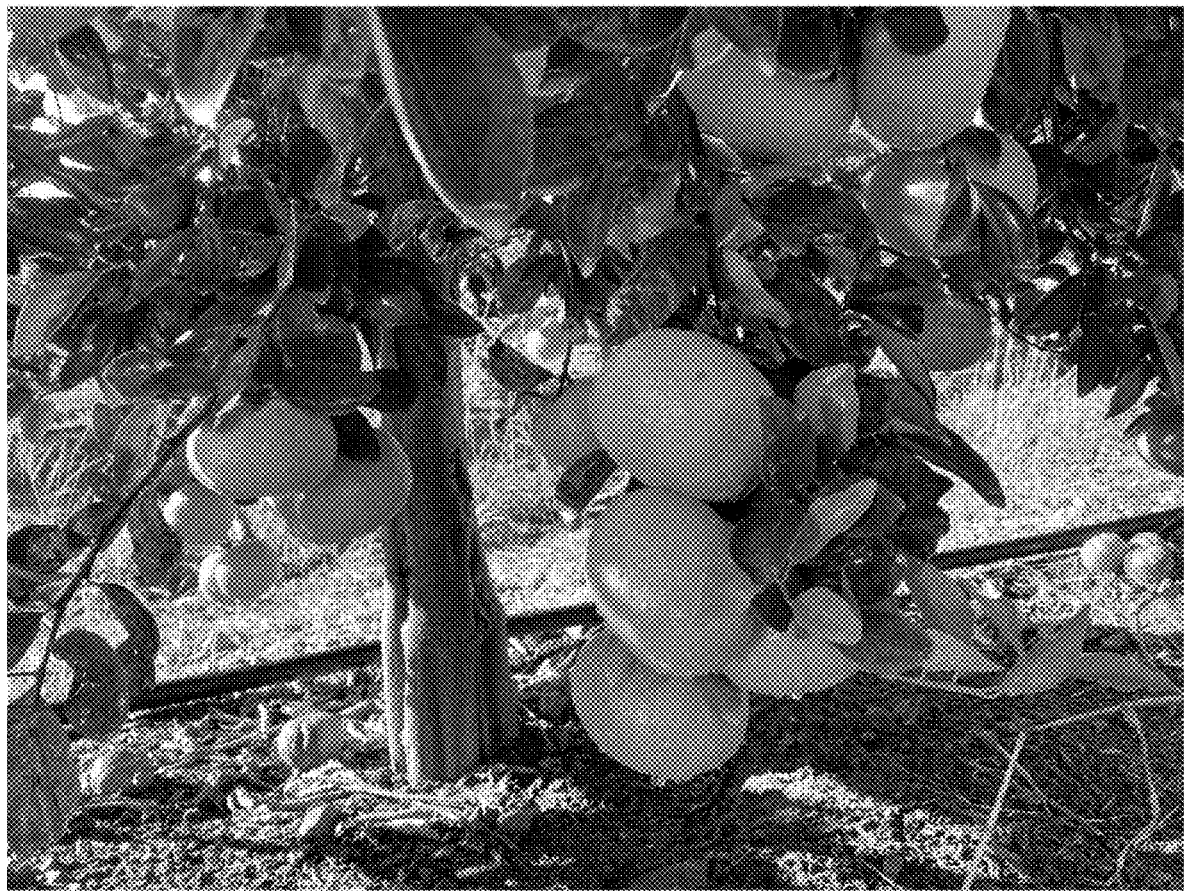
FIG. 3 shows whole fruit on a tree of '12C009' along with typical leaf morphology.

The following descriptions set forth the distinctive characteristics of '12C009'. Unless where otherwise noted, the data that define these characteristics are based on observations taken from '12C009' plants that were four years old, grown on 'Troyer' (unpatented) rootstock in a subtropical environment at Mundubbera, Australia. Color designations, color descriptions, and other phenotypical descriptions may deviate from the stated values and descriptions depending upon variation in environmental, seasonal, climatic and cultural conditions. '12C009' has not been observed under all possible environmental conditions. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family.*—Rutaceae.
*Botanical.*—*Citrus reticulata.*
*Common name.*—Mandarin.
*Variety name.*—'12C009'.

Tree:

*Ploidy.*—Diploid.
*Size.*—Trees have a medium to large stature, similar to 'Ellendale' and 'Murcott'.
*Height.*—3.8 m.
*Width.*—3.7 m.
*Vigor.*—Trees grow vigorously when young but early and heavy cropping helps to restrain subsequent vigor.
*Growth habit.*—Elliptic to oblong.
*Density.*—Canopy is light to medium in density resulting from long branches with sometimes low crotch angles.
*Bearing.*—Productive from an early age with no evidence of alternate bearing.

Trunk:

*Trunk diameter.*—21.5 cm at 30 cm above graft.
*Trunk texture.*—Finely raised.
*Trunk color.*—RHS N200C (Grey).

Branches:

*Crotch angle.*—Major branches at 45-50-degree crotch angle.
*Branch length.*—1.3 to 1.7 m.
*Branch texture.*—Smooth becoming finely raised on older branches.
*Branch color.*—RHS N200C (Grey).
*Thorn prevalence.*—Occasional on some branches, varying with age of growth within the tree canopy; low-vigor growth on older wood has only rudimentary (<2 mm) thorns, similar to what is seen on many existing commercial mandarin cultivars.
*Thorn length* (*vigorous shoots*).—12 mm.
*Thorn width at base* (*vigorous shoots*).—2.5 mm.
*Thorn color.*—RHS 138A (Green).

Leaves:

*Size* (*lamina average*).—Length: 65 mm. Width: 39 mm. L/W ratio: 1.7.
*Arrangement.*—Alternate.
*Type.*—Simple.
*Shape.*—Obovate.
*Color of upper surface.*—RHS 139A (Green).
*Color of lower surface.*—RHS 137C (Green).
*Thickness.*—Regular and consistent with commercial mandarin cultivars.
*Shape.*—Obovate.
*Blade margin.*—Crenate.
*Apex shape.*—Obtuse, emarginated at tip.
*Base shape.*—Acute.
*Texture of upper* (*adaxial*) *surface.*—Glabrous, glossy.
*Texture of lower* (*abaxial*) *surface.*—Glabrous.
*Venation.*—Prominent on lower surface with 1° midrib and 2° laterals raised, 3° and 4° interlaterals weakly developed.
*Midrib color.*—RHS 146A (Yellow-Green).
*Petiole length.*—10 mm.
*Petiole diameter.*—2 mm.
*Petiole color.*—RHS 146A (Yellow-Green).

*Petiole wings*.—Rudimentary; linear, extending half the length of the petiole from the lamina, seldom more than 1 mm wide.

*Color of petiole wing* (*upper surface*).—RHS 139A (Green).

*Color of petiole wing* (*lower surface*).—RHS 137C (Green).

*Petiole attachment*.—Articulate, brevipetiolate.

Flowers:

*Type*.—Hermaphroditic.

*Blooming period*.—Commencing ~25th August with full bloom ~24th September in Queensland, Australia.

*Length*.—13 mm.

*Diameter*.—6 mm.

*Flower petals*.—Number: 5. Color of upper and lower surface: RHS 155B (white). Oil glands: Present on external surface. Length: 11 mm. Width: 4 mm. Shape of apex: Obtuse. Shape of base: Truncate. Margin: Entire. Arrangement within bud: Imbricate. Calyx: Small.

*Fragrance*.—Typical of mandarin.

*Reproductive organs*.—Fertility: Self-fertile. Pollen amount: Moderately abundant. Pollen fertility: Low (assessed via aceto-carmine staining). Number of stamens per flower: 20. Anther color: RHS 12B (Yellow). Filament color: RHS 155B (White). Pollen color: RHS 12C (Yellow).

Fruit:

*Axial diameter*.—87 mm.

*Apical diameter*.—53 mm.

*Weight*.—196 g.

*General shape in profile*.—Obloid.

*Shape in transverse section*.—Somewhat angular.

*Shape of fruit base*.—Truncate, occasionally with wrinkles.

*Shape of fruit apex*.—Truncate.

*Neck*.—Absent.

*Fruit surface texture*.—Smooth.

*Color of fruit surface* (*epicarp*).—RHS 28A (Orange-red).

*Color of fruit flesh* (*mesocarp*).—RHS 25A (Orange).

*Segment length*.—49 mm.

*Segment width*.—28 mm.

*Adherence of mesocarp to endocarp*.—Weak and peels away cleanly.

*Navel*.—Absent.

*Areola*.—Generally absent but occasionally grooved.

*Rind thickness*.—3.3 mm.

*Segment number*.—10-12.

*Harvest window*.—Late-season: end-July (southern hemisphere subtropics).

*Juice soluble solid*.—12.4°Brix (end-July).

*Juice acidity*.—0.95% citric acid equivalent (end-July).

*Fruit storage*.—Fruit stored for 42 days at 5° C. retained their appearance and eating quality. Fruit subjected to a 41 day simulated supply chain regime (30 days at 1.5° C., followed by 2 days at 25° C., followed by 2 days at 5° C., and finally 7 days at 25° C.) only developed off-flavors if they had been coated with a shellac-based wax (carnauba), and un-waxed fruit did not develop off-flavors.

*Seeds*.—0-5 per fruit.

*Seed shape*.—Ovoid-clavate.

*Seed length*.—13 mm.

*Seed width*.—7 mm.

*Seed fresh weight*.—0.3 g.

*Cotyledon color*.—RHS 155A (White).

*Seed type*.—Polyembryonic.

*Alternaria brown spot reaction*.—Susceptible.

What is claimed is:

1. A new and distinct mandarin tree called '12C009' as illustrated and described herein.

* * * * *